United States Patent
John et al.

(10) Patent No.: US 6,235,944 B1
(45) Date of Patent: May 22, 2001

(54) PRODUCTION OF SECONDARYALKOXY-1-ALKENES

(75) Inventors: Thomas V. John, Yardley, PA (US); Chitoor S. Subramaniam; Zheng Wang, both of East Brunswick, NJ (US); Richard J. Kucera, Jr., Hasbrouck Heights, NJ (US)

(73) Assignee: Creanova Inc., Somerset, NJ (US)

( * ) Notice: Subject to any disclaimer, the term of this patent is extended or adjusted under 35 U.S.C. 154(b) by 0 days.

(21) Appl. No.: 09/234,572

(22) Filed: Jan. 21, 1999

(51) Int. Cl.$^7$ .................................................... C07C 41/28
(52) U.S. Cl. ......................... 568/667; 568/587; 568/689; 568/691
(58) Field of Search .................... 568/667, 691, 568/687, 689

(56) References Cited

U.S. PATENT DOCUMENTS

| | | | |
|---|---|---|---|
| 3,072,727 | 1/1963 | Howard et al. ........................ | 260/611 |
| 4,506,102 | * 3/1985 | Kaufhold et al. ..................... | 568/667 |
| 5,399,778 | 3/1995 | Steffen et al. ........................ | 568/591 |
| 5,401,885 | 3/1995 | Subramaniam et al. .............. | 568/595 |

OTHER PUBLICATIONS

Roelofsen, D.P. & Van Bekkum, H.: *Synthesis*, 1972, 419–420, No Month Provided.

Howard, W.L. & Lorette, N.B.; J. Org. Chem. 1960, 25/525, No Month Provided.

MacKenzie, C.A.; Stocker, J.H., J. Org. Chem. 1955, 20/1695, No Month Provided.

Gassman, P.g.; Burns, S.J.; J.H Org. Chem. 1988, 53, 5576 No Month Provided.

Gassman P.g.; Burns, S.J.; Pfister, K.B.; Org. Chem. 1993, 58, 1449 No Month Provided.

Katritzky, A.R.; Bayuk, S. I.; Rachwal, S; *Synthesis* 1991, 279. No Month Provided.

Cookson, R.C.; Singh, P. J.; *Chem. Soc. C 1971*, 1477 No Month Provided.

Lindsay, D.G.; Reese, C. B.; *Tetrahedron* 1965, 21, 1673 No Month Provided.

Patwarthan, S.A.; Dev, S; *Synthesis*, 1974, 348 No Month Provided.

Wohl, R.A.; *Synthesis* 1974, 38 No Month Provided.

* cited by examiner

*Primary Examiner*—Rosalynd Keys
(74) *Attorney, Agent, or Firm*—Abelman, Frayne & Schwab; Thomas E. Spath

(57) ABSTRACT

The present invention relates to a general synthesis for producing secondaryalkoxy-1-alkenes in commercial quantities in good yields by reacting cyclic and acyclic ketones and the corresponding alcohol with a secondary alkyl orthoformate ester in the presence of an acid catalyst, a Lewis acid, ferric chloride being preferred, and recovering the produce as a liquid of high purity.

15 Claims, No Drawings

PRODUCTION OF SECONDARYALKOXY-1-ALKENES

FIELD OF THE INVENTION

The invention relates to a process for the production of secondaryalkoxy-1-alkenes.

BACKGROUND OF THE INVENTION

Secondaryalkoxy-1-alkenes have utility as intermediates in the preparation of pharmaceutical compounds. Methods for the preparation of alkoxy alkenes, have been reported in the prior art. However, none of them provides a general procedure for the preparation of secondaryalkoxy-1-alkenes from cyclic and acyclic ketones. The methods disclosed are limited to the production of primaryalkoxy alkenes and teach the acid-catalyzed elimination of a primary alcohol group from a dialkyl ketal.

As used herein, ketal means a cyclic or acyclic ketone that is subjected to a reaction with an alcohol to form a 1,1-dialkoxyalkane, the latter also referred to as ketone acetals. This definition is more specific, and is to be distinguished from terminology employed in the technical literature where ketal and acetal are sometimes used interchangeably. Thus, a ketone R'R"C=O is thus reacted with 2 R'"—OH to produce the ketal R'R"C(OR'")$_2$ and water.

Several researchers have reported on reaction systems that included the formation of secondaryalkoxy-1-alkenes. Roelofsen et al. disclose a reaction scheme for producing de-sec-alkyl ketals and reported the observation of an equilibrium side reaction in which a secondaryalkoxy-1-cyclohexene was produced as an undesired by-product. *Synthesis*, August 1972, pp. 419–420.

Howard et al. in an article entitled "Ketals of Monohydric Secondary Alcohols", Journal of Organic Chemistry, April 1960, pp. 525–30, describe at p. 526, first column, work by Reichle who reportedly obtained diisopropyl ketals from cyclic ketones and triisopropyl orthoformate. MacKenzie et al. reported the formation of a primaryalkoxy alkene during the transformation of cyclohexanone into its diethyl ketal using triethyl orthoformate as a reactant. However, repeating this reaction scheme employing sec-tributyl orthoformate in place of triethyl orthoformate failed to produce a second-aryalkoxy cycloalkene. Gassman et al. reported a general method to synthesize alkoxy alkenes (enol ethers) from ketals/acetals, which involved treatment of an appropriate ketal/acetal with a 10–75% molar excess of trimethylsilyl triflate and a 20–90% molar excess of N,N-diisopropylethylamine.

Katritzky et al. reported a method for the preparation of ketone enol ethers with both primary and secondaryalkoxy groups. However, the process disclosed requires the intermediate preparation of a benzotriazoyl derivative and a laborious work-up resulting in the generation of a large quantity of undesirable by-products that must be disposed of with the expenditure of additional time and resources.

It is also known from U.S. Pat. No. 5,401,885 to prepare dialkoxycycloalkanes by reacting a cycloalkanone, an iminoether hydrochloride and a secondary alkanol.

It is therefore an object of this invention to provide as a general synthesis, a one-step method to convert cyclic and acyclic ketones into their corresponding secondaryalkoxy-1-alkenes.

It is another object of this invention to provide a process that can produce commercial quantities of alkoxy-1-alkenes economically and with a minimum of undesirable by-products.

SUMMARY OF THE INVENTION

The present invention provides a process for producing secondaryalkoxy-1-alkenes of the structure (A) and (A') as described below:

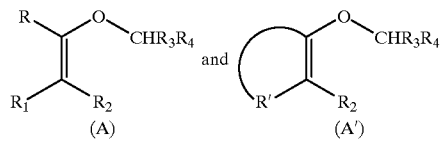

employing the reactants:

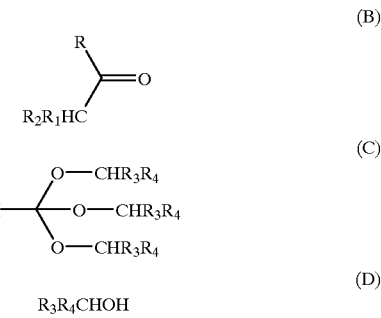

where in (A), $R_1$ and $R_2$ each independently represent a hydrogen atom or a monovalent hydrocarbon group with from 1 to 10 carbon atoms; R, $R_3$ and $R_4$ each independently represent a monovalent hydrocarbon group with from 1 to 10 carbon atoms which can have a substituent; and where in (A'), R and $R_1$ are coupled together to form the R', ring where the ring contains a total of 5–8 carbon atoms, and $R_2$, $R_3$ and $R_4$ are as described above.

Using the process of the invention, the desired secondaryalkoxy-1-alkenes are prepared by reacting acyclic or cyclic ketone of the structure (B) with an orthoester having the structure (C) and an alcohol (D) in the presence of an acid catalyst, wherein R, $R_1$, $R_2$, $R_3$ and $R_4$ have the same meaning as defined above. The formation of these secondaryalkoxy-1-alkenes is accomplished by the direct transformation of the desired ketone without the isolation of an intermediate ketal.

The present process can be used to economically produce commercial quantities of secondaryalkoxy-1-alkenes of high purity, (e.g., greater than 99%), in very good yields which typically exceed 95%. The exothermic reaction can be initiated at ambient temperatures, and in the presence of, or without the use of a solvent—i.e., the use of a solvent is optional. Unlike the processes of the prior art, the present invention proceeds under mild reaction conditions, produces minimum waste, and requires no complex techniques to isolate and recover the end product.

DETAILED DESCRIPTION OF THE INVENTION

The secondaryalkoxy-1-alkenes having the structures (A) and (A'), as described above, are prepared by reacting acyclic or cyclic ketones having the structure (B), second-aryalkyl orthoformate esters of the structure (C) and an alkanol $R_3R_4CH$—OH of structure (D) and in the presence of an acid catalyst. The catalysts that can be used include sodium and potassium bisulfates and their monohydrate salts, methanesulfonic acid, sulfuric acid, p-toluenesulfonic acid and ferric chloride, with ferric chloride being the preferred catalyst. Furthermore, these reactions can be performed with or without the use of a solvent, and preferably without the use of a solvent, at temperatures from −20 to 150° C., preferably from 20 to 80° C. The method of the present invention is preferably conducted in an inert gas atmosphere, such as nitrogen or argon, in order minimize the hazards associated with the highly flammable reactants.

There is no particular limitation to the ketones that can be used in the method of the present invention. The ketones can contain a double bond, and include a substituent. Examples of ketones containing double bonds include isophorone, cyclohexenone; substituents can include, but are not limited to, halogen atoms, aryl, alkyl and alkoxy groups. Preferred ketones include, but are not limited to, 3-pentanone, acetophenone, cyclopentanone, cyclohexanone, isophorone, cycloheptanone, cyclooctanone and x'-acetophenone, where x' is a halogen, alkyl or other substituent on the aromatic ring.

Preferred orthoformate esters used in the process of the present invention include, but are not limited to, 2-propyl, 2-butyl, 2-isopentyl and 3-pentyl orthoformate. There is no particular limit to the amount of the orthoester, alcohol or cyclic ketone used in the reaction; however, the amounts of each reactant should be controlled to minimize the production cost of the desired secondaryalkoxy cycloalkene product.

The molar ratio of ketone and the orthoformate ester can be from about 1:1 to about 1:3 and preferably from 1:1 to abut 1:1.1, that is, from approximately equimolar quantities to a slight excess of either the orthoformate ester or the ketone are used.

As used herein, the acid that is added as a catalyst should be understood to include compounds that are Lewis acids such as $FeCl_3$, $ZnCl$, and $MgCl_2$. The preferred acid catalysts are mild acids, such as ferric chloride, potassium and sodium bisulfates and their monohydrates; however sulfuric acid, p-toluenesulfomic acid and methanesulfomic acid are also useful in the practice of the invention. The preferred Lewis acid catalyst is reagent grade ferric chloride, also known as iron (III) chloride. The acid catalyst is added in an amount that is effective to cause the reaction to proceed at an optimum rate. As will be understood by one of ordinary skill in the art, the amount of catalyst to be added can be readily determined and will vary with the choice of the catalyst, the individual reactants, ambient temperature conditions, and other parameters conventionally considered. In order to minimize impurity levels and the volume of waste material that must be treated, the catalyst is added in the range of from about 0.001 mol (or 1 mmol) to about 0.1 mol of catalyst per mol of ketone or orthoformate ester. Importantly, the activity of the catalyst useful in the practice of the invention is not diminished by the presence of alcohol, or by traces of water, so that the reactants do not have to be specially dried before use. The present invention therefore makes it possible to produce secondaryalkoxy vinyl ethers of the general formula (A) and (A') in high yields without causing a side reaction.

A solvent is not required in the process, but it is possible to use a solvent when the solvent does not inhibit the reaction leading to the desired enol ether product. Preferred solvents include, but are not limited to isopropanol, 2-butanol, 2-isopetanol, 3-pentanol; ethers such as diethyl ether, diisopropyl ether, dibutyl ether; and saturated aliphatic hydrocarbons such as hexane, cyclohexane and toluene. Solvents such as alcohols may be used to solubilize some catalysts, e.g., $NaHSO_4$, $KHSO_4$ and $FeCl_3$.

The process of the present invention is generally conducted at atmospheric pressure or under reduced pressure, preferably within a range of 3 mmHg to 760 mmHg. The reaction temperature, which is suitably set depending on the reaction pressure, generally falls within a range of −20° C. to 150° C., and most preferably falls within the range of 20° C. to 80° C. In the preferred practice of the invention, the reaction is initiated by mixing the reactants at ambient temperature, allowing the temperature to rise in response to the reaction's exotherm, and then providing external heating, as by a hot water or steam, to increase the temperature.

In the large-scale commercial practice of the invention the alcohols, formates, solvents and other by-products can be recovered as separate fractions of the distillates, thereby providing additional economies and reducing waste disposal and treatment requirements.

Other aspects and advantages of the present invention will become apparent from the following examples that are provided for illustration and are not to be construed as limitations of the invention. In all of the examples that follow, the reactions were conducted under an inert atmosphere of nitrogen gas and the reaction vessel was purged with nitrogen. The purities reported were determined by GC analysis.

EXAMPLE 1

A mixture of 190.3 g (1 mol) triisopropyl orthoformate, 98.15 g (1 mol) of cyclohexanone and 6.00 g (0.10 mol) of isopropanol was placed in a three-neck round bottom flask and cooled to about 5° C. in an ice bath. The mixture was stirred and 0.4 g (2 mmol) of reagent grade iron (III) chloride was added. Upon addition of the $FeCl_3$ catalyst, the temperature of the mixture rose to about 15–20° C., indicating that the reaction was proceeding. The mixture was stirred at 20° C. until gas-chromatographic ("GC") analysis indicated completion of the reaction. The by-products isopropyl formate and isopropanol were removed by distillation under reduced pressure. The remaining residue was subsequently distilled to provide 1-isopropoxy-1-cyclohexene (bp 34° C. @3 mm Hg) as a colorless liquid; the yield was 92% with a purity exceeding 99%.

EXAMPLE 2

A mixture of 98.16 grams (1 mol) of cyclohexanone, 195.2 grams (1.03 mol) of triisopropyl orthoformate and 6.00 grams of isopropanol (0.1 mol) was stirred in a 500 ml three-neck round bottom flask. To this mixture, at room temperature (25° C.), 1.36 grams (0.014 mol) of concentrated sulfuric acid was slowly added to initiate the exothermic reaction. The reaction temperature rose to 40° C. due to the exotherm, and the mixture was heated and maintained at 60° C. for about 3 hours. The progress of the reaction was monitored by GC until the cyclohexanone content was less than 0.5%. The isopropanol and isopropyl formate were distilled off under reduced pressure until the pot temperature reached a maximum of 100° C. After cooling it to room temperature, the reaction mixture was neutralized with potassium iso-propoxide. The mixture was then heated under reduced pressure to remove unreacted cyclohexanone. The product 1-isopropoxy-1-cyclohexene, was recovered as a clear liquid; the yield was 85% with a purity exceeding 99%.

EXAMPLE 3

To a mixture at room temperature containing 196.32 grams (2 mol) of cyclohexanone, 390.4 grams (2.06 mol) of triisopropyl orthoformate and 12.00 grams of isopropanol (0.2 mol), was added 7.6 grams (0.055 mol) of sodium hydrogensulfate monohydrate. The reaction was exothermic and upon addition of the catalyst, the temperature of the reaction mixture rose to 35° C., and was heated and maintained at 60° C. for 1 hour. The progress of the reaction was monitored by GC until the cyclohexanone content dropped to less than 2%. The isopropanol and isopropyl formate were distilled off under reduced pressure until the reaction mixture's temperature reached a maximum of 100° C. The reaction mixture was cooled to room temperature and filtered to remove sodium hydrogensulfate monohydrate (recovered). The pH value of the filtrate was adjusted to about 7~8 by adding 0.8 gram of potassium iso-propoxide. The mixture was then heated under reduced pressure to remove unreacted cyclohexanone. The product, 1-isopropoxy-1-cyclohexene was isolated by distillation as a clear liquid; the yield was 81.7% with a purity exceeding 98%.

EXAMPLE 4

A mixture containing 116.2 g (0.5 mol) of tri(2-butyl) orthoformate, 49.10 g (0.5 mol) of cyclohexanone and 3.7 g (0.05 mol) of 2-butanol was stirred at room temperature (25° C.) and 0.2 g (1 mmol) of reagent grade iron (III) chloride was added. The temperature of the reaction mixture rose to about 35° C. due to the exotherm and was heated and maintained at about at 50° C. until gas-chromatographic analysis indicated that the reaction was complete. After removing the by-products 2-butyl formate and 2-butanol by distillation under reduced pressure, the resulting residue was subsequently distilled to provide 1-(2-butoxy)-1-cyclohexene (bp 86° C. @2 mm Hg) as a colorless liquid; the yield was 89.4% with a purity exceeding 99%.

EXAMPLE 5

A mixture of 84.12 grams (1 mol) of cyclopentanone, 195.2 grams (1.03 mol) of triisopropyl orthoformate and 60 grams of isopropanol (1 mol) was stirred in a 500 ml three-neck round bottom flask at room temperature. To this mixture, 3.8 g (0.028 mol) of sodium hydrogensulfate monohydrate was added, and the temperature of the reaction mixture was heated and maintained at 40° C. for about one hour. The progress of the reaction was monitored by GC until the cyclopentanone content was reduced to less than 2%. The isopropanol and isopropyl formate were distilled off under reduced pressure while the temperature of the reaction mixture was increased to a maximum of 65° C. The reaction mixture was cooled to room temperature and the pH value was adjusted to about 7~8 by adding about 0.2 gram of potassium iso-propoxide. The mixture was then heated under reduced pressure to remove unreacted cyclopentanone and 64 grams (0.51 mol) of 1-isopropoxy-1-cyclopentene was isolated as a clear liquid at a yield of 51%. The purity of the product exceeded 98%.

EXAMPLE 6

To a mixture of 56.0 grams (0.50 mol) of cycloheptanone, 107.0 grams (0.56 mol) of triisopropyl orthoformate and 44 grams of isopropanol (0.73 mol) in a 500 ml three-neck round bottom flask was added 2.8 grams (0.020 mol) of sodium hydrogensulfate monohydrate. Upon catalyst addition, the reaction temperature rose to 45° C., and was heated and maintained at 50° C. for about 5 hours. The progress of the reaction was monitored by GC until the ketone concentration was below 2%. The isopropanol and isopropyl formate by-products were removed by distillation under reduced pressure while the temperature of the reaction mixture was increased to a maximum of 60° C. The reaction mixture was cooled to room temperature and the pH value adjusted to about 7~8 by adding 0.4 of gram potassium iso-propoxide. The mixture was then heated under reduced pressure to remove unreacted cycloheptanone and 1-isopropoxy-1-cyclopentene was isolated as a clear liquid at a yield of 60.1%. The purity of the product exceeded 98%.

EXAMPLE 7

To a stirred mixture of 49.08 grams (0.50 mol) of 3-pentanone, 133.23 grams (0.7 mol) of triisopropyl orthoformate and 30.5 grams of isopropanol (0.5 mol) in a 500 ml three-neck round bottom flask was added 4.76 grams (0.034 mol) of sodium hydrogensulfate monohydrate. Due to the exothermic nature of the reaction, upon the catalyst addition the temperature of the reaction mixture rose to, and was maintained at 40° C. for 26 hours. The isopropanol and isopropyl formate were removed by distillation under reduced pressure and the temperature of the reaction mixture was increased to a maximum of 100° C. The reaction mixture was then heated under reduced pressure to remove unreacted 3-pentanone and 3-isopropoxy-2-pentene (as a mixture of E and Z isomers) was isolated as a colorless liquid at a yield of 67% with a purity exceeding 98%.

We claim:
1. A method for the production of secondaryalkoxy-1-alkenes having the structure (A):

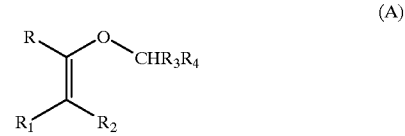

(A)

where $R_1$ and $R_2$ each independently are a hydrogen atom or a monovalent hydrocarbon radical having from 1 to 10 carbon atoms; R, $R_3$ and $R_4$ each independently are a substituted or unsubstituted monovalent hydrocarbon group having from 1 to 10 carbon atoms; or secondaryalkoxy-1-alkenes having the structure (A'):

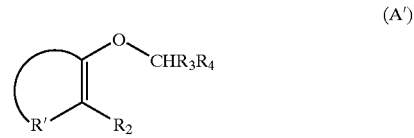

(A')

where R and R' are joined to form a ring R', which ring contains 5 to 8 carbon atoms, where the method comprises the steps of:

(a) forming a reaction mixture of a cyclic or an acyclic ketone of the formula:

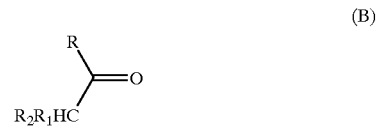

(B)

a secondaryalkyl orthoformate ester of the formula:

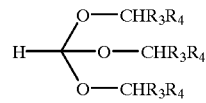

(C)

where R, $R_1$, $R_2$, $R_3$ and $R_4$ are as defined above for acyclic ketones and $R_2$ is hydrogen for cyclic ketones, and an alkanol of the formula:

$R_3R_4CH{-}OH$, where $R_3$ and $R_4$ are as defined above;

(b) adding to the reaction mixture of step (a) an effective amount of an acid catalyst;

(c) agitating the reaction mixture while monitoring the progress of the reaction; and (d) recovering the secondaryalkoxy-1-alkene from the reaction mixture as a liquid.

2. The method of claim 1 where the alkanol is selected from the group consisting of isopropanol and 2-butanol.

3. The method of claim 1 in which the ketone (B) is selected from the group consisting of 3-pentanone, acetophenone, cyclopentanone, cyclohexanone, isophorone, cycloheptanone and cyclooctanone.

4. The method of claim 3 where the ketone (B) is selected form the group consisting of cycloheptanone, cyclohexanone, cycloheptonone and 3-pentanone.

5. The method of claim 1 where the substituents $R_3$ and $R_4$ are selected from the group consisting of methyl, ethyl and propyl.

6. The method of claim 5 where the substituents $R_3$ and $R_4$ are selected from the group consisting of methyl and ethyl.

7. The method of claim 1 where the acid catalyst added in step (b) is selected from the group consisting of ferric chloride, zinc chloride, magnesium chloride, sodium bisulfate, sodium hydrogen sulfate monohydrate, potassium bisulfate, potassium hydrogen sulfate monohydrate, methane sulfonic acid, p-toluene sulfonic acid and sulfuric acid.

8. The method of claim 7 where the acid catalyst is ferric chloride.

9. The method of claim 1 where the reaction mixture is initiated under conditions of ambient pressure and temperature.

10. The method of claim 1 where the recovery of the secondaryalkoxy-1-alkene includes the further step of distilling the reaction mixture to remove by-products of the reaction.

11. An improved process for the synthesis of secondaryalkoxy-1-alkenes of the formula:

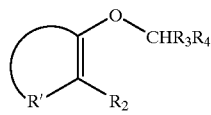

(A')

where R' is a substituted or unsubstituted cyclic member formed from 5 to 8 carbon atoms. $R_2$ is a hydrogen atom or a monovalent hydrocarbon radical having from 1 to 10 carbon atoms, and $R_3$ and $R_4$ each independently are a substituted or unsubstituted monovalent hydrocarbon group having from 1 to 10 carbon atoms, where the method comprises:

(a) providing a reaction mixture comprising
(i) a cyclic ketone of the formula:

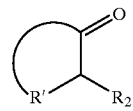

where R' and $R_2$ correspond to the substituents defined above for (A')

(ii) a secondary orthoformate ester of the formula

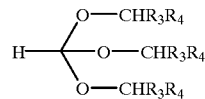

where $R_3$ and $R_4$ are as defined above for (A'), and (iii) an alkanol of the formula $R_3R_4CHOH$, where $R_3$ and $R_4$ are defined as above for (A');

(b) adding to the reaction mixture of step (a) an effective amount of an acid catalyst;

(c) agitating the reaction mixture while monitoring the progress of the reaction; and (d) recovering the cyclic secondaryalkoxy-1-alkene (A') from the reaction mixture as a liquid.

12. The method of claim 11 where R' is an unsubstituted cyclic member with 6 carbon atoms.

13. The method of claim 11 where the substituents $R_3$ and $R_4$ are selected from the group consisting of methyl, ethyl and propyl.

14. The method of claim 11 where the acid catalyst added in step (b) is selected from the group consisting of ferric chloride, zinc chloride, magnesium chloride, sodium bisulfate, sodium hydrogen sulfate monohydrate, potassium bisulfate, potassium hydrogen sulfate monohydrate, methane sulfonic acid, p-toluene sulfonic acid and sulfuric acid.

15. The method of claim 14 where the acid catalyst is ferric chloride.

\* \* \* \* \*